United States Patent
Barfoed

[11] Patent Number: 6,066,486
[45] Date of Patent: May 23, 2000

[54] **METHOD OF HYDROLYZING CHOLESTEROL ESTERS BY USING A *PSEUDOMONAS FRAGI* CHOLESTEROL ESTERASE**

[75] Inventor: Martin Barfoed, Birkerød, Denmark

[73] Assignee: Novo Nordisk A/S, Bagsvaerd, Denmark

[21] Appl. No.: 08/525,688

[22] PCT Filed: Mar. 30, 1994

[86] PCT No.: PCT/DK94/00137

§ 371 Date: Sep. 27, 1995

§ 102(e) Date: Sep. 27, 1995

[87] PCT Pub. No.: WO94/23052

PCT Pub. Date: Oct. 13, 1994

[30] Foreign Application Priority Data

Apr. 2, 1993 [DK] Denmark ................................. 395/93

[51] Int. Cl.[7] ...................................... C12N 9/16
[52] U.S. Cl. ......................... 435/198; 435/196; 435/136; 435/155
[58] Field of Search ..................... 435/198, 196, 435/136, 155

[56] References Cited

FOREIGN PATENT DOCUMENTS 0 204 284  12/1986  European Pat. Off. .
0 205 208  12/1986  European Pat. Off. .
WO 93/10224  5/1993  WIPO .

OTHER PUBLICATIONS

Chemical Abstract—Abstract No. 3955, Wakako et al., Biochim. Biophys. Acta. (1991).
Chemical Abstract—Abstract No. 216788, Sumitomo Chemical Co. (1993).
Chemical Abstract—Abstract No. 36573, Buchert, et al., Appl. Microbiol. Biotechnol. (1988).
WPIDS—WPIDS Accession No. 78–60989A, Toyobo (1978).

*Primary Examiner*—Leon B. Lankford, Jr.
*Attorney, Agent, or Firm*—Steve T. Zelson, Esq.; Valeta Gregg, Esq.

[57] ABSTRACT

A cholesterol esterase from *Pseudomonas fragi* FERM BP-1051 can be used to hydrolyze cholesterol ester. The enzyme can be used in cleaning compositions.

10 Claims, 1 Drawing Sheet

```
SEQUENCE LISTING

<160> NUMBER OF SEQ ID NOS: 1

<210> SEQ ID NO 1
<211> LENGTH: 27
<212> TYPE: PRT
<213> ORGANISM: Pseudomonas fragi

<400> SEQUENCE: 1

Ala Asp Asn Tyr Ala Ala Thr Arg Tyr Pro Ile Ile Leu Val His Gly
1               5                   10                  15

Leu Thr Gly Thr Asp Lys Tyr Ala Gly Val Leu
            20                  25
```

METHOD OF HYDROLYZING CHOLESTEROL ESTERS BY USING A *PSEUDOMONAS FRAGI* CHOLESTEROL ESTERASE

CROSS-REFERENCE TO RELATED APPLICATIONS

This application is a 371 of PCT/DK94/00137 filed Mar. 30, 1994, which is incorporated herein by reference.

TECHNICAL FIELD

The present invention relates to a method of hydrolysing a cholesterol ester. More specifically, the invention relates to use of a cholesterol esterase enzyme obtainable from a strain of *Pseudomonas fragi*.

BACKGROUND ART

It is well known that some of the members belonging to the genus Pseudomonas possess the ability to produce cholesterol esterase, other members possess the ability to produce lipase, and that furthermore some members possess the ability to produce both types of enzymes.

In U.S. Pat. No. 4,283,494 a lipase derived from *Pseudomonas alcaligenes*, able to become activated by bile salts, and having cholesterol esterase activity is described.

In a study by Smirnov et. al. [Smirnov, V. V.; Kornyushenko, O. N.; Bioko, O. I.; Kolesova, E. A.; Govseeva, N. N.; Endt, V. P.; and Kiprianova, E. A.; Mikrobiologicheskii Zhurnal (Kiev); 42 (5), 1980, 566–570], a total of 591 strains of 25 species of bacteria belonging to the genus Pseudomonas were studied for their ability to synthesize extracellular cholesterol esterase. Only individual strains of *Ps. aeruginosa, Ps. pseudoacaligenes, Ps. fluorescens, Ps. putida,* and *Ps. maltophilia* (3.4% of the studied cultures) had cholesterol esterase activity. Lipolytic activity was found in *Ps. aureofaciens* (in 100% of the studied strains), *Ps. cepacia* (in 75%), *Ps. maltophilia* (in 60%), *Ps. fluorescens* (in 13.3%), and *Ps. aeruginosa* (in 60%).

From this study it is noticed that none of the *Ps. fragi* cultures examined were able to produce cholesterol esterases.

SUMMARY OF THE INVENTION

According to the present invention it has now been found that strains of *Pseudomonas fragi* are able to produce extracellular cholesterol esterase. Moreover, it has surprisingly been found that the enzyme component responsible for the cholesterol esterase activity is also the component responsible for the lipase activity.

Accordingly, the invention relates to the use of a cholesterol esterase obtainable from a strain of *Ps. fragi*, i.e. to a method of hydrolysing a cholesterol ester by treating the ester with said cholesterol esterase enzyme. The method of the invention is particular useful for the treatment of eggs, in processes for hydrolysis of resin in pulp, and in processes for hydrolysis or synthesis of sterols or lanolin.

In another aspect, the invention provides a cleaning composition comprising a cholesterol esterase obtainable from a strain of *Ps. fragi*.

BRIEF DESCRIPTION OF THE DRAWING

The present invention is further illustrated by reference to the accompanying drawing, in which.

DETAILED DISCLOSURE OF THE INVENTION

Figure 1:
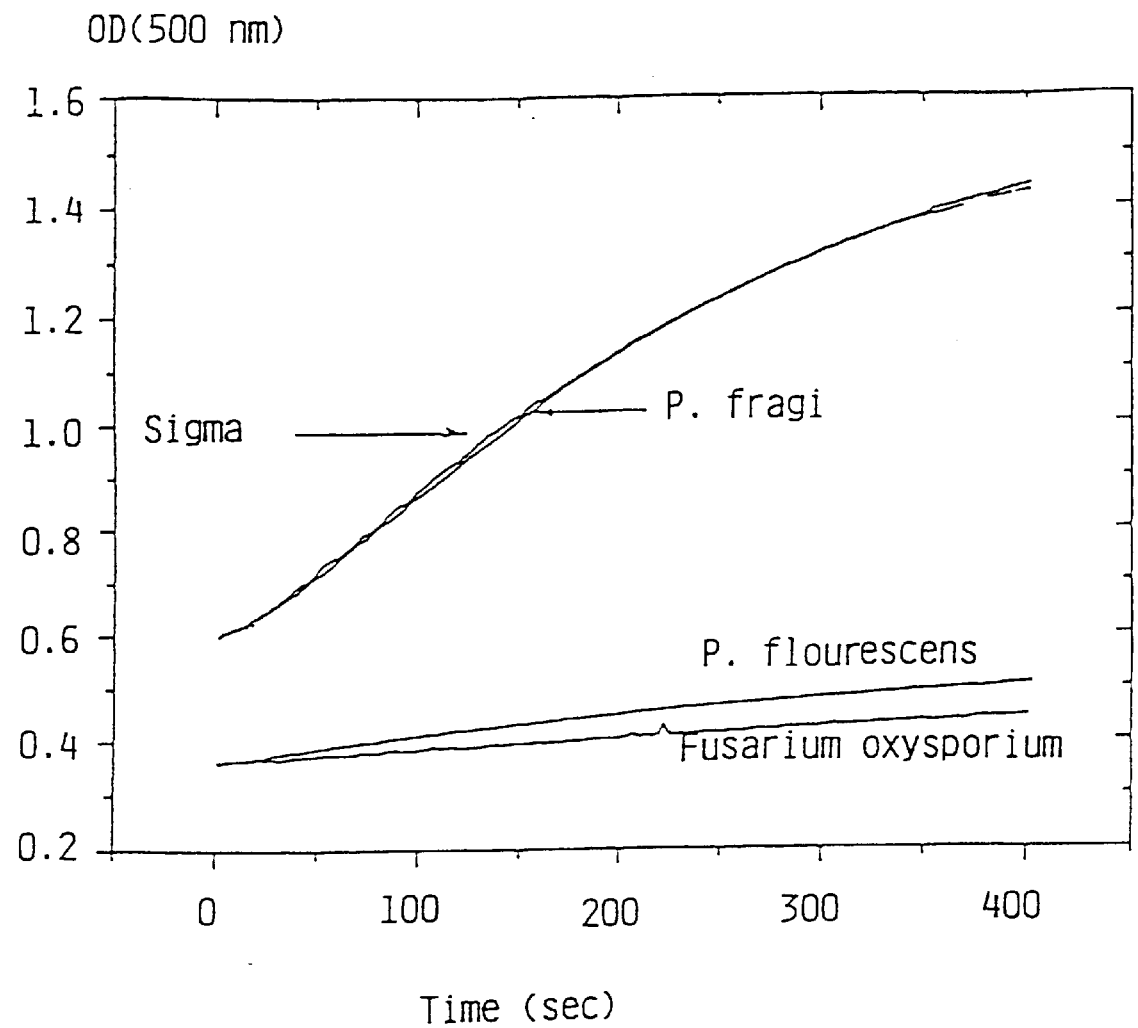
FIG. 1 shows the kinetic curves (absorbance versus time) for various enzymes as obtained by spectrophotometric determination, cf. Example 2.

Surprisingly, it has now been found that strains of *Pseudomonas fragi* possess the ability to produce enzymes having cholesterol esterase activity and that the enzyme responsible for the cholesterol esterase activity is identical to the enzyme responsible for the lipase activity, i.e. the very same protein possesses lipase activity as well as cholesterol esterase activity.

Accordingly, the present invention relates to a method of hydrolysing a cholesterol ester comprising treating the cholesterol ester with a cholesterol esterase enzyme obtainable from a strain of *Pseudomonas fragi*.

In a preferred embodiment, the cholesterol esterase is Lipase B from *Ps. fragi*, available from WAKO Pure Chemical Industries, Ltd., Japan, order No. 126-02931, and derived from the strain *Ps. fragi* 22.39B, FERM BP-1051, or a mutant or a variant thereof.

In a more preferred embodiment, the cholesterol esterase has the N-terminal amino acid sequence identified by SEQ ID No: 1 of the sequence listing attached to this specification.

Thus it should be noted that the enzyme used in the method of the invention having cholesterol esterase activity as well as lipase activity may be described e.g. as a cholesterol esterase acting lipase or a lipase acting cholesterol esterase.

The cholesterol esterase used in the method of the invention may be obtained by cultivation of a cholesterol esterase producing strain of *Ps. fragi*, preferably the strain *Ps. fragi* 22.39B, FERM BP-1051, or a mutant or a variant thereof, in a suitable nutrient medium, containing carbon and nitrogen sources and inorganic salts, followed by recovery of the desired enzyme.

A highly purified lipase was obtained from the above lipase preparation Lipase B 126-02931, supplied by WAKO Pure Chemical Industries Ltd. Japan, by the methods described in Example 1 of this specification. By amino acid degradation, the N-terminal amino acid sequence of this enzyme was found to be the one identified as ID No. 1 in the sequence listing attached to this specification. By the method described in Example 2 of this specification it was shown that this enzyme also possesses cholesterol esterase activity.

The cholesterol esterase used in the method of the invention may also be obtained by recombinant DNA technology. By expression of a protein with the dual lipase and cholesterol esterase activity, special advantages may be achieved. The recombinant cholesterol esterase may be obtained e.g. by using the methods described in International Patent Application published as WO92/05249 which is hereby incorporated by reference.

Thus, the present invention further relates to a method of hydrolysing a cholesterol ester comprising treating the cholesterol ester with a cholesterol esterase enzyme which has immunochemical properties identical to a cholesterol esterase derived from *Pseudomonas fragi* FERM BP-1051, and has substantial cholesterol esterase activity.

Both cholesterol esterases and lipases have widespread industrial applications.

Accordingly, in a further aspect, the invention also relates to the use of a cholesterol esterase obtainable from alipase producing strain of Ps. fragi for hydrolysis of eggs, i.e. to a method for treatment of eggs with cholesterol esterase.

In a yet further aspect, the invention relates to use of a cholesterol esterase obtainable from a lipase producing strain of Ps. fragi in processes for hydrolysis of resin in pulp, i. e tp a method for treatment of resin-containing papermaking pulp. Mechanical pulping, alone or combined with a gentle chemical treatment, is widely used in the manufacture of pulps. These processes occur at pH in the range of 4–9, and the components of the wood undergo relatively small chemical changes. The pulp, therefore, has a considerable content of triglycerides, esters and waxes from resin.

Residual resin may cause problems during the subsequent processing and/or use of the pulp. Exemplary, agglomerated resin may cause paper breakage during paper manufacture or during printing as well as lowering the paper quality. It is known that the hydrophobic part of resin contains considerable amounts of triglycerides and other esters. It is, therefore, desirable to hydrolyse these, as the hydrolysis products are more easily removed in aqueous systems.

Processes for hydrolysis of resins in pulps have been described in e.g. International Patent Application Nos. PCT/DK92/00115 and PCT/DK92/00137, or International Patent Publication Nos. WO 92/07138 and WO 92/13130, and may be carried out essentially as described therein.

In a yet further aspect, the method of the invention relates to the hydrolysis or synthesis of sterols or lanolin by treating a cholesterol ester with a cholesterol esterase obtainable from a lipase producing strain of Ps. fragi. Such a cholesterol esterase may advantageously be used also in the manufacture of leather for degreasing of pelt, for the hydrolysis of lanolin in the wool industry, and for hydrolysis/synthesis of sterols/lanolin, e.g. lanosterol for use in cosmetics.

The invention also provides a cleaning composition comprising a cholesterol esterase obtainable from a lipase producing strain of Ps. fragi. Especially cleaning compositions formulated as gels, i.e. gel cleaning agents, may be used for industrial hard surface cleaning, particularly in slaughterhouses and other food industry.

Specific gel cleaning agents may be obtained as described in e.g. Research Disclosure 340 August 1992, disclosure No. 34045 (Gel Cleaner Containing an Enzyme).

The following examples further illustrate the invention, and they are not intended to be in any way limiting to the scope of the invention as claimed.

EXAMPLE 1

Purification

A Ps. fragi lipase preparation, Lipase B 126-02931, supplied by WAKO Pure Chemical Industries Ltd. Japan, and derived from the strain Ps. fragi 22.39B, deposited as FERM BP-1051, and disclosed in EP-A-0 204 284, was purified to homogeneity in the following way.

The lipase was passed through a S-sepharose cation exchanger with 50 mM sodium acetate buffer at pH 6. The lipase did not bind to the matrix.

The effluent containing lipase activity was adjusted to 0.8 M sodium acetate and applied on Toyopearl Butyl column, equilibrated with 0.8 M sodium acetate. The column was washed with 0.8 M sodium acetate, until the colour containing material had disappeared. The lipase bound to the matrix was eluted with 50% of ethanol, concentrated and separated from ethanol by dialysis.

The lipase was then subjected to a High Performance Q-sepharose anionic exchanger (Pharmacia) at pH 7 using 50 mM Tris Acetate buffer, and purified to homogeneity (as evidenced on SDS-PAGE).

The purified lipase had a specific activity of 8000 LU/OD280 as determined by the following assay for lipase activity:

A substrate for lipase was prepared by emulsifying glycerine tributyrat (MERCK) using gum-arabic as emulsifier.

Lipase activity was assayed at pH 7 using pH stat method. One unit of lipase activity (LU) was defined as the amount needed to liberate one micromole fatty acid per minute.

N-Terminal Amino-Acid Analysis

The N-terminal amino-acid sequence of the above lipase/cholesterol esterase was determined using standard methods for obtaining and sequencing peptides [Findlay & Geisow (Eds.), Protein sequencing—a practical approach, 1989, IRL Press].

The lipase/cholesterol esterase was purified as described above. In order to remove the Tris buffer, the purified lipase/cholesterol esterase was applied to a Superdex 200 TM column, using a 50 mM sodium acetate buffer, pH 6.

The N-terminal amino acid sequence was found to be as follows (SEQ ID No:1 of the attached sequence listing):

Ala-Asp-Asn-Tyr-Ala-Ala-Thr-Arg-Tyr-Pro-Ile-Ile-Leu-Val-His-Gly-Leu-Thr-Gly-Thr-Asp-Lys-Tyr-Ala-Gly-Val-Leu-

EXAMPLE 2

Assay for Cholesterol Esterase Activity

An enzymatic assay for cholesterol esterase activity was developed, and the cholesterol esterase activity of some lipases was examined.

The analysis is based on the following three coupled reactions:

| 1) Cholesterol oleate | --(1)--> | Cholesterol + Oleic acid |
| 2) Cholesterol + $O_2$ + $H_2O$ | --(2)--> | $H_2O_2$ + Cholesterone |
| 3) $H_2O_2$ + 4-Aminoantipyrine(red) | --(3)--> | $2H_2O$ + 4-Amino-antipyrine (ox) |

Enzymes involved:
(1) Cholesterol esterase (to be assayed)
(2) Cholesterol oxidase
(3) Peroxidase The redox reaction of 4-aminoantipyrine is followed by a change in absorbance at 500 nm with an extinction coefficient (E) of 6.89.

Conditions and Reagents:

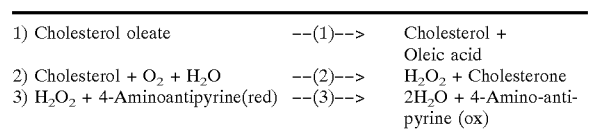

| pH: | 7.0 |
|---|---|
| Temperature (T): | 37° C. |
| Buffer: | 0.4 M $KH_2PO_4$; pH 7.0; 37° C. (54.4 mg/ml) |
| Substrate: | 0.0086 M cholesterol oleate (5.6 mg/ml). Dissolve 56.0 mg cholesterol oleate in 1.0 ml polyoxyethylene-9-lauryl-ether. Add a small stirring bar and stir gently. While stirring add 9.0 ml of hot (>50° C.) saline solution |

-continued

| | |
|---|---|
| | (0.9% w/w). Leave the solution at room temperature. |
| Other: | 15% (w/w) taurocholic acid, Na salt (150 mg/ml); |
| | 1.75% (w/w) 4-aminoantipyrine (17.5 mg/ml); |
| | 6% (w/w) phenol (60 mg/ml) |
| Coupling enzymes: | Cholesterol oxidase, Sigma ® C-1512 (1 mg protein/ml). |
| | Peroxidase, Sigma ® P-8250 (39.5 purpurogallin units/ml). |
| Enzyme: | Cholesterol esterase (0.02–0.4 u/ml) |

Procedure:

Into a 1 cm standard silica cuvette; buffer, 2.07 ml; taurocholic acid, 0.10 ml; peroxidase, 0.10 ml; and substrate, 0.50 ml; was pipetted and mixed by inversion.

Then phenol, 0.10 ml, was added and mixed by inversion.

Next 4-aminoantipyrine, 0.05 ml, and cholesterol oxidase, 0.03 ml, were added, and a baseline at 500 nm was obtained.

Ultimately cholesterol esterase, 0.05 ml, was added, and ΔOD at 500 nm (dA/dt) was obtained.

Calculation of Cholesterol Esterase Units:

$$\text{Units/mg solid} = \frac{OD/\min}{6.89 \times (\text{mg enxyme/ml reaction mixture})}$$

One cholesterol esterase unit is defined as the amount of enzyme that will hydrolyse 1 μmole of cholesterol oleate per minute at pH 7.0 and 37° C.

Enzymes Examined

The enzymes examined are shown in Table 1 below. To ensure that only one enzyme protein was present, highly purified enzyme preparations were applied, cf. the purification method described in Example 1.

The enzymes examined (cf. Table 1) were dosed on an equal OD basis. As reference was used a cholesterol esterase from Sigma®. Of this enzyme, 50 μl of a solution with OD=0.077, approx. 0.077 mg/ml, was used.

All enzymes were scanned for 400–600 sec., and the above mentioned gradient dA/dt was calculated for the interval 30–120 sec. From these results the activities shown in Table 1 were calculated. The spectrophotometric determinations are shown in FIG. 1.

TABLE 1

Calculated Activities

| Sample | Cholesterol esterase activity units/mg |
|---|---|
| Cholesterol esterase, Sigma ® C-1403 | 18.2 ± 1.3 |
| *Ps. fragi* cholesterol esterase/lipase*) | 20.2 ± 0.5 |
| *Ps. flourescens* lipase | 3.3 |
| Candida A lipase | 2.5 |
| Candida B lipase | 2.7 |
| *Candida cyldracia* lipase | 1.4 |
| Guinea pig lipase | 0 |
| *Fusarium oxysporum* lipase | 1.7 |

*)Obtained according to Example 1

From Table 1 it appears that only the reference from Sigma® and the *Ps. fragi* cholesterol esterase/lipase obtained according to example 1 have any significant cholesterol esterase activity. The lipase derived from *Ps. flourescens* did not show significant cholesterol esterase activity.

I claim:

1. A method for hydrolyzing a cholesterol ester comprising treating the cholesterol ester with a cholesterol esterase enzyme obtainable from a strain of *Pseudomonas fragi*, wherein the strain is *Pseudomonas fragi* 22.39B, FERM BP-1051, or a mutant or a variant thereof.

2. A method according to claim 1, wherein the cholesterol esterase is obtainable from the strain *Pseudomonas fragi* 22.39B, FERM BP-1051, or a mutant or a variant thereof.

3. A method according to claim 1, wherein the cholesterol esterase has the N-terminal amino acid sequence of SEO ID NO:1.

4. A method according to any of the claim 1 for the treatment of eggs.

5. A method according to any of the claim 1 for the treatment of resin-containing papermaking pulp.

6. A method according to any of the claim 1 for hydrolysis or synthesis of sterols or lanolin.

7. A method of hydrolysing a cholesterol ester comprising treating the cholesterol ester with a cholesterol esterase enzyme which has immunochemical properties identical to a cholesterol esterase derived from *Pseudomonas fragi* FERM BP-1051, and has substantial cholesterol esterase activity.

8. A cleaning composition comprising a cholesterol esterase obtainable from a strain of *Pseudomonas fragi*.

9. A composition according to claim 8, wherein the cholesterol esterase is obtainable from the strain *Pseudomonas fragi* 22.39B, FERM BP-1051, or a mutant or a variant thereof.

10. A composition according to claim 8, wherein the cholesterol esterase has the N-terminal amino acid sequence of SEQ ID NO:1.

* * * * *

UNITED STATES PATENT AND TRADEMARK OFFICE
CERTIFICATE OF CORRECTION

PATENT NO. : 6,066,486
DATED : May 23, 2000
INVENTOR(S) : M. Barfod

Page 1 of 1

It is certified that error appears in the above-identified patent and that said Letters Patent is hereby corrected as shown below:

<u>Column 6,</u>
Line 52, claim 3, delete "Seo" and insert --SEQ --

Signed and Sealed this

Twenty-eighth Day of August, 2001

Attest:

*Nicholas P. Godici*

NICHOLAS P. GODICI
*Attesting Officer*   *Acting Director of the United States Patent and Trademark Office*